United States Patent
Yamakawa

(10) Patent No.: US 11,504,044 B2
(45) Date of Patent: Nov. 22, 2022

(54) ELECTROCARDIOGRAM WAVEFORM MEASUREMENT SYSTEM AND ELECTROCARDIOGRAM WAVEFORM MEASUREMENT METHOD

(71) Applicant: Quadlytics Inc., Kyoto (JP)

(72) Inventor: Toshitaka Yamakawa, Kumamoto (JP)

(73) Assignee: QUADLYTICS INC., Kyoto (JP)

( * ) Notice: Subject to any disclaimer, the term of this patent is extended or adjusted under 35 U.S.C. 154(b) by 310 days.

(21) Appl. No.: 16/646,481

(22) PCT Filed: Sep. 14, 2018

(86) PCT No.: PCT/JP2018/034221
§ 371 (c)(1),
(2) Date: Mar. 11, 2020

(87) PCT Pub. No.: WO2019/054492
PCT Pub. Date: Mar. 21, 2019

(65) Prior Publication Data
US 2020/0268269 A1   Aug. 27, 2020

(30) Foreign Application Priority Data

Sep. 15, 2017   (JP) .............................. JP2017-177818

(51) Int. Cl.
*A61B 5/316*   (2021.01)
*A61B 5/021*   (2006.01)
(Continued)

(52) U.S. Cl.
CPC .......... *A61B 5/316* (2021.01); *A61B 5/02116* (2013.01); *A61B 5/282* (2021.01); *A61B 5/352* (2021.01); *A61B 5/6804* (2013.01)

(58) Field of Classification Search
CPC ..... A61B 5/316; A61B 5/02116; A61B 5/282; A61B 5/352; A61B 5/6804
See application file for complete search history.

(56) References Cited

U.S. PATENT DOCUMENTS

| 9,757,581 | B2 * | 9/2017 | Sullivan | ............... | A61N 1/3918 |
| 2011/0288605 | A1 * | 11/2011 | Kaib | .................. | A61B 5/4836 |
| | | | | | 607/5 |

(Continued)

FOREIGN PATENT DOCUMENTS

WO     2015115441 A1     8/2015

OTHER PUBLICATIONS

International Search Report dated Nov. 27, 2018 for PCT/JP2018/034221 and English translation.

*Primary Examiner* — Gary Jackson
*Assistant Examiner* — Alexander M Eisenberg
(74) *Attorney, Agent, or Firm* — Lucas & Mercanti, LLP

(57) ABSTRACT

An electrocardiogram waveform measurement system is configured to be suitable for measuring an electrocardiogram waveform with high precision using multiple electrodes provided to an article of clothing. A measurement unit performs measurement in a state in which multiple fabric electrodes are grouped into multiple channels. A signal measured by the electrodes for each channel is evaluated in a two-dimensional manner based on the number of times an R wave is detected by an R wave processing unit in a predetermined period of time and a degree of data concentration in a dynamic range acquired by a degree-of-concentration calculation unit. A channel selection unit selects the optimum channel.

3 Claims, 4 Drawing Sheets

(51) Int. Cl.
*A61B 5/00* (2006.01)
*A61B 5/352* (2021.01)
*A61B 5/282* (2021.01)

(56) References Cited

U.S. PATENT DOCUMENTS

2012/0302860 A1* 11/2012 Volpe .................. A61B 5/7221
600/512
2014/0323894 A1* 10/2014 Zhang .................. A61B 5/7246
600/518

* cited by examiner

[FIG. 1]
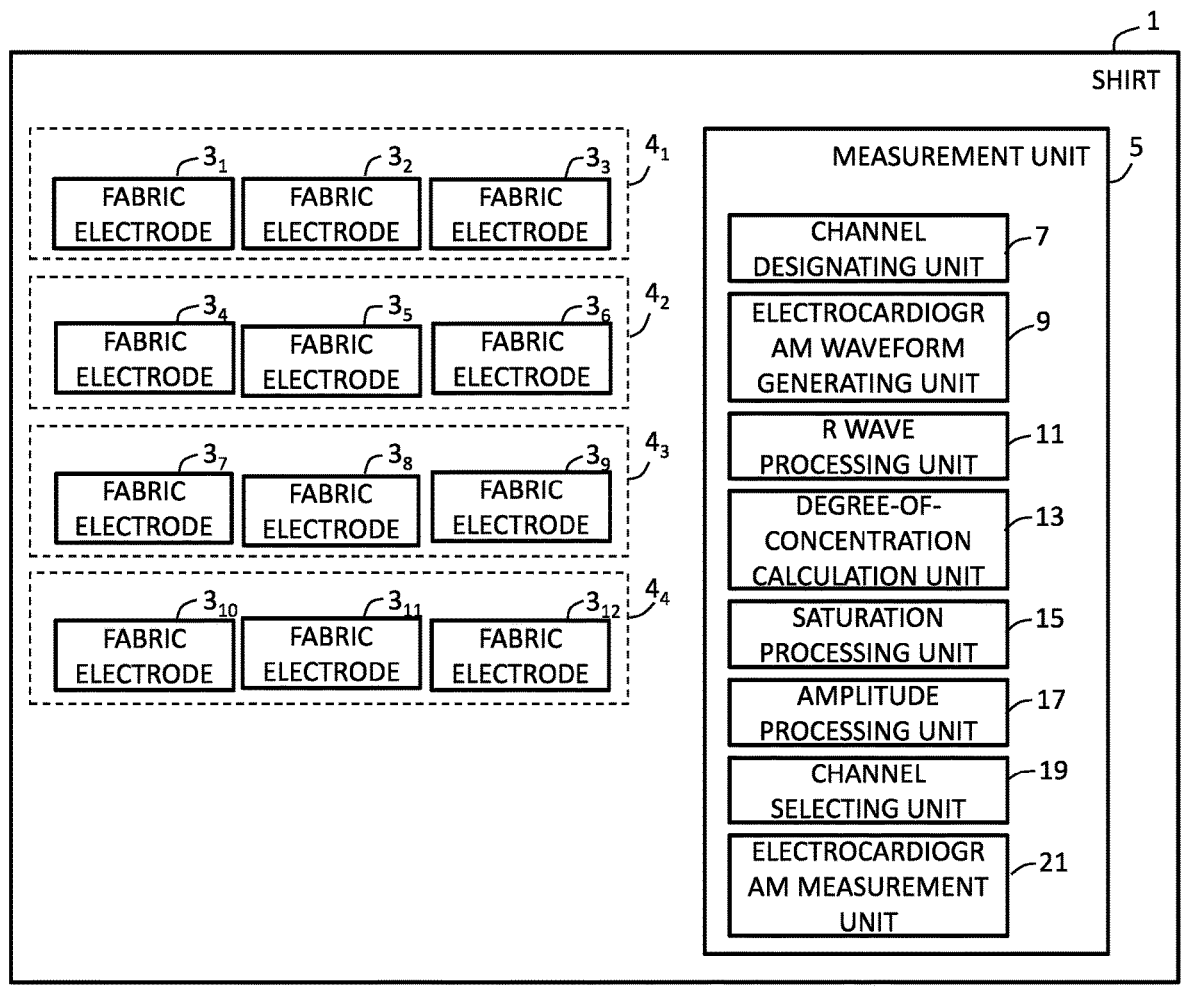

[FIG. 2]
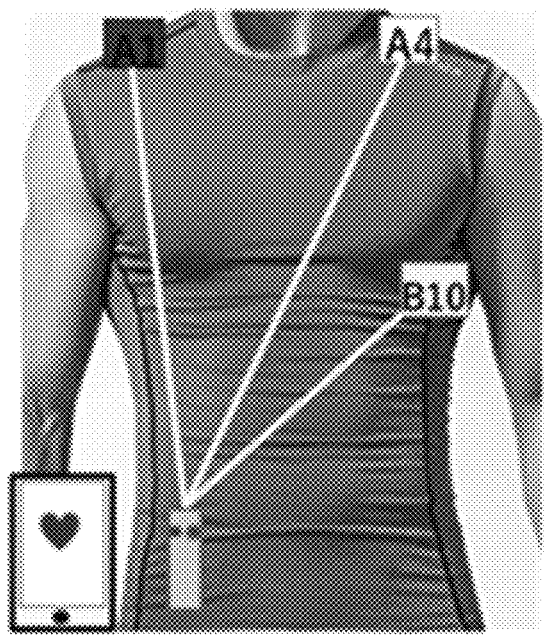
(a)
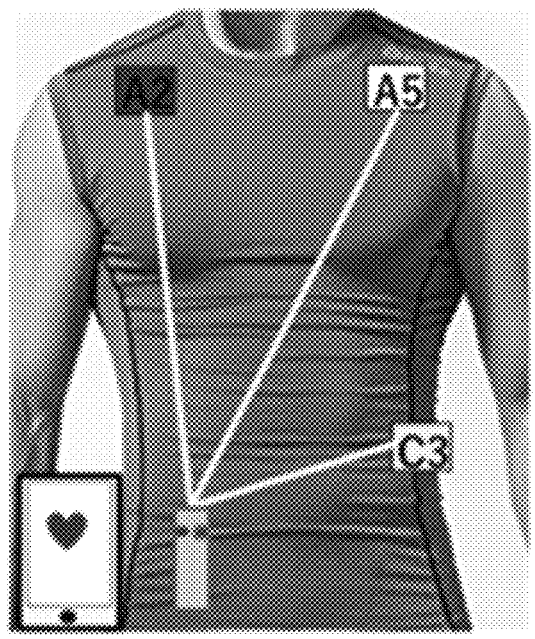
(b)
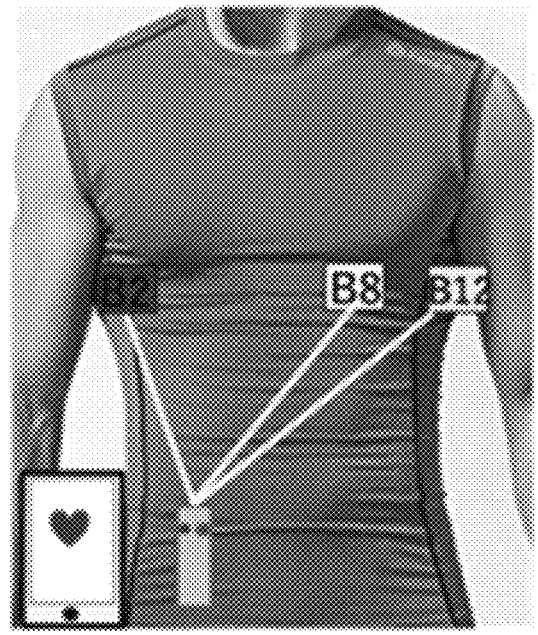
(c)
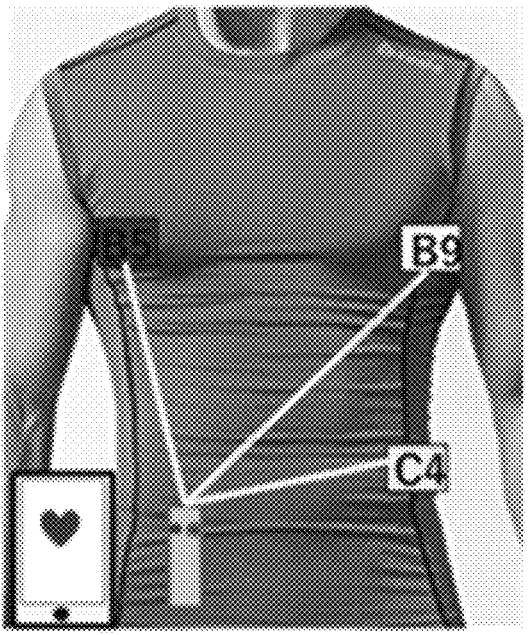
(d)

[FIG. 3]
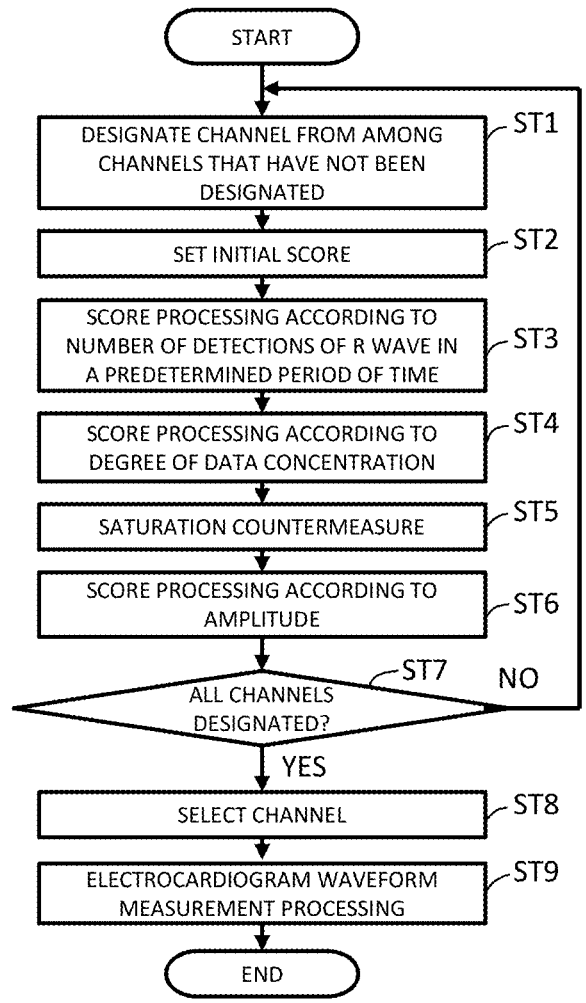

[FIG. 4]
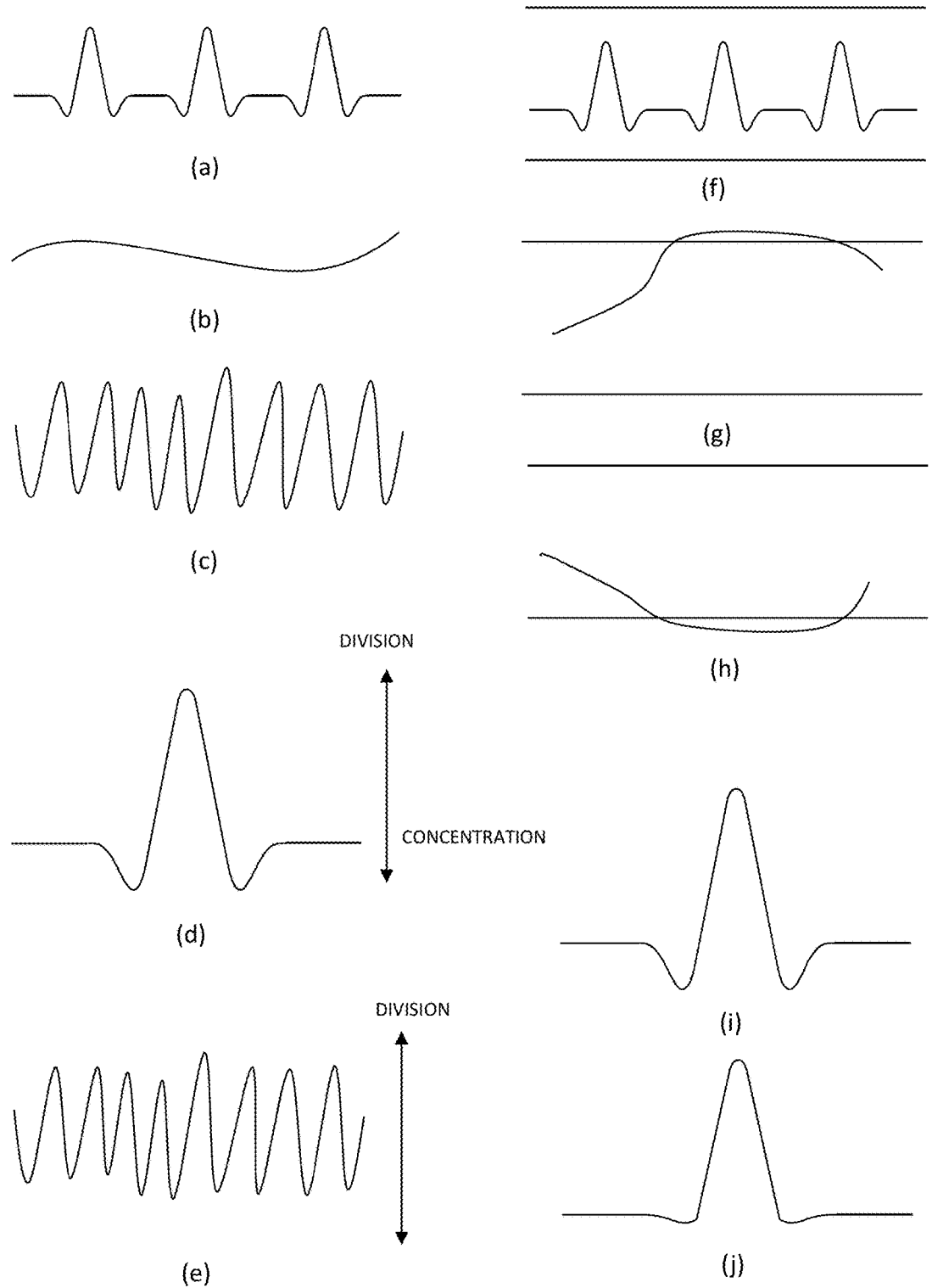

ELECTROCARDIOGRAM WAVEFORM MEASUREMENT SYSTEM AND ELECTROCARDIOGRAM WAVEFORM MEASUREMENT METHOD

CROSS REFERENCE TO RELATED APPLICATION

This Application is a 371 of PCT/JP2018/034221 filed on Sep. 14, 2018 which, in turn, claimed the priority of Japanese Patent Application No. 2017-177818 filed on Sep. 15, 2017, both applications are incorporated herein by reference.

TECHNICAL FIELD

The present invention relates to an electrocardiogram waveform measurement system and an electrocardiogram waveform measurement method. Particularly, the present invention relates to an electrocardiogram waveform measurement system or the like that measures an electrocardiogram waveform using multiple fabric electrodes fixed to a shirt.

BACKGROUND ART

In order to obtain effective and highly reliable information using a wearable sensor for supporting a medical diagnosis or health care, an electrocardiogram measurement is employed as an essential method. A commercially available method for measuring a photoelectric pulse wave on a subject's wrist provides only insufficient precision. Accordingly, other measurement methods have been proposed as prospective methods, examples of which include a measurement method employing disposable electrodes and a measurement method employing shirt-type electrocardiogram electrodes. In Patent document 1, a measurement method is described in which a shirt is provided with multiple electrodes, with one or two configured as different electrodes and the remaining electrodes configured as an indifferent electrodes (positive reference potential electrodes), so as to detect a biological signal.

CITATION LIST

Patent Literature
[Patent Document 1]
International Publication WO 2015/115441 pamphlet

SUMMARY OF INVENTION

Technical Problem

However, in a case of measuring the RRI using disposable electrodes according to conventional techniques, in some cases, such an arrangement has a problem of the occurrence of redness or inflammation of the skin, or a problem of the occurrence of adhesive paste marks.

Furthermore, it is known that even in such a case in which measurement is performed using a shirt provided with such multiple electrodes, such an arrangement has a problem in that the optimum electrode layout changes depending on individual difference such as the physique of the wearer. With shirt-type electrodes, the shirt size and electrode positions are configured to be fixed. Accordingly, with measurements using such shirt-type electrodes, individual differences are likely to have a large effect. This leads to a large problem in that, in about 10% of subjects, such an arrangement provides an electrocardiogram with a very small amplitude, or such an arrangement provides an inverted characteristic wave.

The sole countermeasure for solving such a problem is to provide a shirt with many electrode members at many positions as in the background art described in Patent document 1. However, in a case of generating a multi-channel electrocardiogram, this leads to a problem of complicated wiring. In a case of providing wireless multiplexing transmission thereof, such an arrangement requires large electric power. Such an arrangement cannot be provided from the viewpoint of wearable size and wearable weight.

Furthermore, conventionally, a specialist supports the measurement. Accordingly, the measurement is performed assuming that all the electrodes arranged at predetermined portions of a shirt are able to detect biological signals as in the background art described in Patent document 1. However, such electrodes provided to a shirt or the like have the potential to cause a problem in that a correct biological signal cannot be detected due to the occurrence of a gap between it and the living subject. Also, due to individual differences, such a correct biological signal cannot necessarily be detected using such an electrode fixed to the shirt. If there will be an increased need in the future for electrocardiogram measurement without involving a specialist so as to provide improved health care, or for a wearable device used for health promotion, and for prevention and early detection of diseases, it is difficult to realize the assumption that the biological signals can be measured via all the multiple electrodes of a shirt-type wearable device. This leads to difficulty in measuring the biological signals using such electrodes.

Accordingly, it is a purpose of the present invention to propose an electrocardiogram waveform measurement system or the like configured to be suitable for measuring an electrocardiogram waveform with high precision using multiple electrodes provided to an article of clothing.

Solution of Problem

A first aspect of the present invention relates to an electrocardiogram waveform measurement system configured to measure an electrocardiogram waveform using multiple electrodes fixed to an article of clothing. The electrocardiogram waveform measurement system comprises: an electrocardiogram waveform generating unit configured to generate an electrocardiogram waveform using measurement values acquired by the electrodes for each of multiple channels with a combination of a part of the multiple electrodes as a channel; an R wave processing unit configured to measure an R wave in the electrocardiogram waveform for each channel; a degree-of-concentration calculation unit configured to calculate a degree of data concentration in a dynamic range of the electrocardiogram waveform for each channel; and a channel selecting unit configured to select a combination of the electrodes to be used to measure the electrocardiogram waveform using the number of times the R wave has been measured by the R wave processing unit and the degree of data concentration calculated by the degree-of-concentration calculation unit.

A second aspect of the present invention relates to the electrocardiogram waveform measurement system according to the first aspect. The electrodes are each configured as a fabric electrode. The electrocardiogram waveform measurement system comprises: a saturation processing unit configured to detect a portion that deviates from the dynamic range; and an amplitude detection unit configured to detect an amplitude of the electrocardiogram waveform. The electrocardiogram waveform generating unit generates an electrocardiogram waveform for each of the combinations using the measurement values acquired in a predetermined period of time by the fabric electrodes. The channel selecting unit selects, from the multiple channels, a channel at which the number of times the R wave has been detected is within a predetermined range, which is detected by the R wave processing unit, with higher priority than a channel at which the number of times the R wave has been detected deviates from a predetermined range. The channel selecting unit selects, from the multiple channels, a channel that exhibits a higher degree of data concentration, which is calculated by the degree-of-concentration calculation unit, with higher priority than a channel that exhibits a lower degree of data concentration. The channel selecting unit selects, from the multiple channels, a channel that does not deviate from a dynamic range, which is detected by the saturation processing unit, with higher priority than a channel that deviates from the dynamic range. The channel selecting unit selects, from the multiple channels, a channel that provides an electrocardiogram waveform having a larger amplitude, which is detected by the amplitude detection unit, with higher priority than a channel that provides an electrocardiogram waveform having a smaller amplitude.

A third aspect of the present invention relates to an electrocardiogram waveform measurement method for measuring an electrocardiogram waveform using multiple electrodes fixed to an article of clothing. The electrocardiogram waveform measurement method comprises: electrocardiogram waveform measuring in which, with a combination of a part of the multiple electrodes as a channel, an electrocardiogram waveform is generated using measurement values acquired by the electrodes for each of multiple channels; R wave processing in which an R wave in the electrocardiogram waveform is measured for each channel; degree-of-concentration calculation in which a degree of data concentration is calculated for each channel in a dynamic range of the electrocardiogram waveform; and channel selecting in which a combination of the electrodes to be used to measure the electrocardiogram waveform is selected using the number of times the R wave has been measured in the R wave processing and the degree of data concentration calculated in the degree-of-concentration calculation.

Advantageous Effects of Invention

The present inventors have found that continuous measurement and analysis of variation of the R wave interval (R-R interval), which is a characteristic wave of an electrocardiogram, allows prediction of epileptic seizures or drowsy driving, screening for sleep apnea syndrome, and early diagnosis of dementia with Lewy bodies, to be supported based on irregularity in the autonomic nervous system. The shirt-type electrode is applied as a wearable health care device, which allows the user to use it in daily life without specialized knowledge. The present invention proposes a combination of the findings of the present inventors and a shirt-type electrode. With such an arrangement, each channel, which is a combination of multiple fabric electrodes, is evaluated in a two-dimensional manner using the time axis and other axes that differ from the time axis, i.e., at least the number of R wave detections and the degree of R wave concentration in the dynamic range. The electrocardiogram waveform is measured using the channel selected based on the evaluation result, thereby allowing the electrocardiogram waveform to be detected with improved detection precision using the multiple electrodes.

For example, in a case in which the electrocardiogram waveforms are detected at multiple channels, there is a large difference between them in the detection precision in the electrocardiogram waveform detection due to the disposition of the heart or the like. With each aspect of the present invention, such an arrangement ensures that, when a given fabric electrode is not in contact with a living subject, such a channel is not selected. Furthermore, when the electrocardiogram waveforms are detected at multiple channels, such an arrangement selects the optimum-layout channel determined depending on individual differences or the like, thereby providing improved detection precision. In actuality, as described later, even in a case of measuring a subject for which it has not been possible to measure the R-R interval at all due to lead setting failure in measuring the electrocardiogram using the shirt-type electrode, such an application according to the present invention provides measurement with extremely high precision. Furthermore, with the second aspect of the present invention, the electrocardiogram waveform is measured giving consideration to the saturation processing and the amplitude, thereby providing the electrocardiogram waveform measurement with improved precision.

Here, channel selecting processing is performed before the electrocardiogram waveform measurement, for example. Also, this arrangement may support electrocardiogram waveform measurement with channel selecting during sleep. For example, the channel may be re-selected when the electrocardiogram waveform measurement accuracy becomes poor due to a change in the subject's orientation when the subject turns over in bed or the like. Also, the channel selection may be periodically performed. A program developed as an example of the present invention is implemented on a compact-size, low-power microcontroller. Accordingly, such a signal processing system can be provided on a compact-size circuit substrate having a size of 3 cm×7 cm, which may be suitably applied to a wearable device.

BRIEF DESCRIPTION OF DRAWINGS

FIG. 1 is a block diagram showing an example of a configuration of an electrocardiogram waveform measurement system according to an embodiment of the present invention.

FIG. 2 is a diagram showing four leads used in an experiment.

FIG. 3 is a flowchart showing an example of the operation of the electrocardiogram waveform measurement system shown in FIG. 1.

FIG. 4 is a diagram showing an example of an electrocardiogram waveform measured by the electrocardiogram waveform measurement system shown in FIG. 1.

DESCRIPTION OF EMBODIMENTS

Description will be made below with reference to the drawings regarding an example of the present invention. It should be noted that the present invention is not restricted to such an example.

EXAMPLE

FIG. 1 is a block diagram showing an example of an electrocardiogram waveform measurement system according to an embodiment of the present invention. In the electrocardiogram measurement system, a shirt 1 is provided with multiple fabric electrodes 3 and a measurement unit 5. Channels 4 are each configured as a combination of multiple fabric electrodes 3 selected from among all the fabric electrodes 3. The measurement unit 5 includes a channel designating unit 7, an electrocardiogram waveform generating unit 9, an R wave processing unit 11, a degree-of-concentration calculation unit 13, a saturation processing unit 15, an amplitude processing unit 17, a channel selecting unit 19, and an electrocardiogram measurement unit 21.

The fabric electrodes 3 and the measurement unit 5 are connected by wiring. The signal detected by each fabric electrode 3 can be measured by the measurement unit 5. FIG. 1 shows an arrangement including twelve fabric electrodes 3 with a combination of three fabric electrodes 3 as one channel. Specifically, FIG. 1 shows an arrangement including twelve fabric electrodes $3_1$, . . . , $3_{12}$, with a combination of the fabric electrodes $3_1$, $3_2$, and $3_3$ as a channel $4_1$, with a combination of the fabric electrodes $3_4$, $3_5$, and $3_6$ as a channel $4_2$, with a combination of the fabric electrodes $3_7$, $3_8$, and $3_9$ as a channel $4_3$, and with a combination of the fabric electrodes $3_{10}$, $3_{11}$, and $3_{12}$ as a channel $4_4$.

A signal can be measured by three fabric electrodes included in a given channel with a given fabric electrode as a ground and with the two other fabric electrodes as a positive electrode and a negative electrode, for example, which can form an electrocardiogram waveform. FIGS. 2A through 2D show leads 1 through 4 used in an experiment described later, and specifically, show the positions of three fabric electrodes included in each channel in a case in which the twelve fabric electrodes are divided into four channels.

FIG. 3 is a flowchart showing an example of the operation of the electrocardiogram waveform measurement system shown in FIG. 1. FIG. 4 shows an example of the electrocardiogram waveform measured by the electrocardiogram waveform measurement system shown in FIG. 1.

The channel designating unit 7 designates one channel from among the channels that have not been designated (Step ST1). Description will be made in the present example in which multiple channels cannot be measured at the same time, and accordingly, the multiple channels are sequentially measured in a one-by-one manner. In order to prevent a score from becoming a negative value in a subsequent score calculation, an initial score of 10,000 is set for the designated channel (Step ST2).

The electrocardiogram waveform generating unit 9 acquires an electrocardiogram waveform using a designated channel. For example, the electrocardiogram waveform generating unit 9 acquires 2,000 samplings of the electrocardiogram waveform with an amplification rate of approximately 30 for 2 seconds using the corresponding lead.

The R wave processing unit 11 adds a value to the score according to the number of times the R wave has been detected in the period of the electrocardiogram waveform acquisition supported by the electrocardiogram waveform generating unit 9 (Step ST3). For example, when the R wave has been detected once in 2 seconds, the R wave processing unit 11 adds 500 to the score. When the number of times the R wave has been detected is equal to or larger than 2 and is equal to or smaller than 5, the R wave processing unit 11 adds 900 to the score. When the number of times the R wave has been detected is equal to 6, the R wave processing unit 11 adds 400 to the score. When the number of times the R wave has been detected is equal to 7, the R wave processing unit 11 adds 300 to the score. When the number of times the R wave has been detected is equal to 8, the R wave processing unit 11 adds 200 to the score. When the number of times the R wave has been detected is equal to 0 or otherwise is equal to or larger than 9, the R wave processing unit 11 does not perform the score addition. FIG. 4A shows a typical example of the electrocardiogram waveform measured for 2 seconds. The R wave represents an electrical flow that occurs when the heart contracts, which is known as a main wave in the electrocardiogram waveform. The interval between the R waves is referred to as the "R-R interval" (RRI). The measurement of the R-R interval is useful for early detection of diseases, health management, or the like. Accordingly, there is an increasing demand for continuous RRI measurement. The number of R waves detected in 2 seconds is on the order of 2 through 5. In contrast, when the R wave has not been detected as shown in FIG. 4B or when a large number of R waves have been detected as shown in FIG. 4C, it can be considered that the electrocardiogram waveform has been detected with poor precision. Accordingly, when a typical heart rate has been detected in 2 seconds, the score is raised. Otherwise, the score is lowered.

The degree-of-concentration calculation unit 13 performs score processing according to the degree of data concentration (Step ST4). For example, the dynamic range of the signal that represents the electrocardiogram waveform is divided into 32 sections. The section including the most signals in 2 seconds is selected. Furthermore, the sections immediately above and immediately below the section with the most signals are selected. A value that matches the number of data signals included in these sections thus selected is added to the score. This processing is performed under an assumption that a stable electrocardiogram waveform is acquired such that it is concentrated in the vicinity of the center of the dynamic range. That is to say, as shown in FIG. 4D, a stable electrocardiogram waveform tends to concentrate at a particular range with variance above and below it. In contrast, as shown in FIG. 4E, an unstable electrocardiogram waveform tends to have data that is distributed over a wide range. Accordingly, the degree-of-concentration calculation unit 13 calculates the degree of data concentration in the dynamic range (i.e., a value that is higher when there is a section in which data concentration occurs in the dynamic range, and is lower when the data is distributed over a wide range), and performs the score calculation based on the degree of data concentration thus calculated.

The saturation processing unit 15 performs saturation countermeasure processing (Step ST5). For example, the saturation processing unit 15 detects a portion in which the signal that represents the electrocardiogram waveform deviates from the dynamic range. When the signal deviates upward, the product of 1 and the number of frames in which the upward deviation has occurred is subtracted from the score. When the signal deviates downward, the product of 5 and the number of frames in which the downward deviation has occurred is subtracted from the score. The initial score 10,000 is determined such that it does not become a negative value even if downward deviation occurs at all times.

The amplitude processing unit 17 detects the amplitude of a signal that represents the electrocardiogram waveform, and performs the score processing according to the amplitude thus detected (Step ST6). For example, after the AD conversion, the amplitude processing unit 17 adds the value obtained by subtracting the minimum value of the electrocardiogram waveform from the maximum value thereof to the score.

The channel designating unit 7 judges whether or not all the channels have been designated (Step ST7). When judgment has been made that all the channels have been designated, the flow proceeds to Step ST8. Otherwise, the flow returns to Step ST1, and one channel is designated from among the channels that have not been designated. Subsequently, the processing in Steps ST2 through ST6 is performed.

In Step ST8, the channel selecting unit 19 selects the channel that exhibits the highest score as the optimum channel. Subsequently, the electrocardiogram measurement unit 21 measures an electrocardiogram waveform by means of the corresponding lead using the channels thus selected (Step ST9).

It should be noted that FIG. 1 shows an arrangement in which the measurement unit 5 is configured as a single apparatus. Also, for example, an apparatus that supports a part of the functions is provided to the shirt 1, and an information processing apparatus such as a smartphone or the like may support the other functions by communicating with the apparatus provided to the shirt 1. Also, each fabric electrode 3 may be included in a single channel. Also, each fabric electrode 3 may be included in multiple channels. Also, in a case in which all the channels can be measured at the same time, instead of selecting each channel and performing the processing for the selected channel, the measurement may be performed for all the channels at the same time so as to calculate the score.

It should be noted that FIG. 3 shows an example in which the channel selecting processing is performed before the electrocardiogram waveform measurement. Also, after the channel selecting processing performed by the channel selecting unit 19, all the score calculation or a part of the score calculation may be performed at all times or periodically for the electrocardiogram waveform measured for the channel selected by a score calculation unit (not shown) included in the electrocardiogram measurement unit 21. Also, when the score thus calculated is high, the channel thus selected is maintained. Conversely, when the score thus calculation becomes low, the channel selecting processing may be performed again. Examples of a case in which the score becomes low include: a case in which the score becomes lower than a predetermined reference value; a case in which the percentage of the score with respect to the score calculated in the first selecting stage becomes a predetermined value or less (e.g., 80%); a case in which the score becomes lower than the score of any one of the other channels that have not been selected; a case in which the rate of the decrease with respect to the score calculated in the immediately previous calculation is equal to or larger than a predetermined rate (e.g., 10%); etc. This arrangement supports electrocardiogram waveform measurement with channel selecting during sleep. Specifically, this arrangement allows the optimum channel to be re-selected when the electrocardiogram waveform measurement accuracy becomes poor due to a change in the subject's orientation when the subject turns over in bed or the like. Also, the channel selecting processing may be periodically performed.

Next, description will be made regarding a verification experiment for evaluating the effectivity of a telemeter (which will be referred to as a "4CH-RRI telemeter" hereafter) having a function of selecting the optimum lead to be used for the RRI measurement from among the four leads shown in FIG. 2, which was performed after the development of the shirt-type fabric electrodes by the present inventors.

The RRI measurement was performed for ten healthy male collage students (average age 19.6, standard deviation±1.11) using the shirt developed by the present inventors and a 4-CH RRI telemeter. The measurement was performed for 5 minutes for the 10 subjects in each of a supine position, a sitting position, an upright position, and while walking (3 km/h). In addition, in order to compare the results, the same measurement was performed using the same shirt and an RRI telemeter that supports the RRI measurement using only the lead 1 (which will be referred to as a "1CH-RRI telemeter" hereafter).

In the measurement for the 10 subjects, when the RRI value was equal to or smaller than 300 ms, when the RRI value was equal to or larger than 1,500 ms, or when the RRI changed by 200 ms or more per beat, judgement was made that the RRI was falsely detected. Otherwise, judgement was made that the RRI was measured normally. Table 1 shows the results calculated with the normal detection rate as the detection rate.

The optimum lead distribution selected by the 4CH-RRI telemeter included sixteen selections of the lead 1, eight selections of the lead 2, seven selections of the lead 3, and nine selections of the lead 4. As a result, the most selected lead was the lead 1, which is typically employed. However, in some cases, other leads were selected. That is to say, it can be confirmed that the optimum lead changes due to a change in physique or movement. Furthermore, there were seven measurements in which the RRI was not detected with the 1CH-RRI telemeter. In contrast, in the measurements using the 4CH-RRI telemeter, the RRI was detected for all the subjects.

The detection rate was compared between the 1CH-RRI telemeter and 4CH-RRI telemeter. As a result, the 1CH telemeter exhibited a higher detection rate in eight measurements. The 4CH telemeter exhibited a higher detection rate in fifteen measurements. The 4CH telemeter and the 1CH telemeter exhibited the same detection rate in seventeen measurements. It can be considered that the reason why there is a difference in the detection rate between them when the 4CH-RRI telemeter selected the lead 1 is that the measurements using the 4CH telemeter and the 1CH telemeter were not performed at the same time.

In Table 1, when the 4CH-RRI telemeter selected a lead that was not the lead 1 and the detection rate provided by the 4CH-RRI telemeter was smaller than that provided by the 1CH-RRI telemeter, the detection rate provided by the 4CH-RRI telemeter is shown by a bold number. With the 4CH-RRI telemeter configured according to the current specifications, the optimum lead is selected in only the startup stage. Accordingly, it can be considered that the poor detection rates shown by the bold numbers in Table 1 were obtained due to changes in the optimum lead that occurred due to movement or the like of the wearer in the measurement.

As described above, the 4CH-RRI telemeter provides a more effective operation than that provided by the 1CH-RRI telemeter. By developing a system configured to automatically re-select the optimum lead during the RRI measurement, and by reviewing the optimum lead selecting process, it can be anticipated that such an arrangement provides a further improved RRI detection rate.

TABLE 1

|  | SUBJECT 1 | | SUBJECT 2 | | SUBJECT 3 | | SUBJECT 4 | | SUBJECT 5 | |
| --- | --- | --- | --- | --- | --- | --- | --- | --- | --- | --- |
|  | 1ch | 4ch | 1ch | 4ch | 1ch | 4ch | 1ch | 4ch | 1ch | 4ch |
| SUPINE POSITION | 100 | 100 | ... | 82.0 | 67.8 | 44.0 | ... | 80.0 | 99.0 | 99.3 |
| SITTING POSITION | 100 | 100 | ... | 70.7 | 92.0 | 98.7 | 94.0 | 53.5 | 95.8 | 90.4 |
| UPRIGHT POSITION | 94.2 | 100 | ... | 96.3 | 96.0 | 93.4 | 98.8 | 92.1 | 97.0 | 100 |
| WHILE WALKING | ... | 44.1 | ... | 44.1 | ... | 42.1 | 26.5 | 42.1 | 68.4 | 86.6 |

|  | SUBJECT 6 | | SUBJECT 7 | | SUBJECT 8 | | SUBJECT 9 | | SUBJECT 10 | |
| --- | --- | --- | --- | --- | --- | --- | --- | --- | --- | --- |
|  | 1ch | 4ch | 1ch | 4ch | 1ch | 4ch | 1ch | 4ch | 1ch | 4ch |
| SUPINE POSITION | ... | 94.5 | 96.7 | 99.0 | 97.7 | 99.0 | 74.0 | 95.3 | 100 | 100 |
| SITTING POSITION | 88.0 | 92.4 | 97.7 | 70.7 | 97.3 | 96.0 | 88.8 | 90.0 | 79.1 | 74.2 |
| UPRIGHT POSITION | 75.0 | 95.5 | 95.0 | 98.0 | 99.5 | 59.7 | 87.3 | 39.9 | 43.5 | 36.3 |
| WHILE WALKING | 14.0 | 27.0 | 82.3 | 100 | 88.6 | 53.0 | 21.7 | 35.2 | 88.7 | 84.7 |

REFERENCE SIGNS LIST

1 shirt, 3 fabric electrode, 4 channel, 5 measurement unit, 7 channel designating unit, 9 electrocardiogram waveform generating unit, 11 R wave processing unit, 13 degree-of-concentration calculation unit, 15 saturation processing unit, 17 amplitude processing unit, 19 channel selecting unit, 21 electrocardiogram measurement unit.

The invention claimed is:

1. An electrocardiogram waveform measurement system configured to measure an electrocardiogram waveform using a plurality of electrodes fixed to an article of clothing, the electrocardiogram waveform measurement system comprising a microcontroller configured to:
    generate an electrocardiogram waveform using measurement values acquired by the electrodes for each of a plurality of channels, each of the plurality of the channels being a combination of a part of the plurality of electrodes;
    count R waves in the electrocardiogram waveform for each channel to acquire a number of the R waves;
    calculate a degree of data concentration in a dynamic range of the electrocardiogram waveform for each channel, wherein the dynamic range is divided into multiple sections; and
    select a combination of the electrodes having a highest score among the plurality of the channels to measure the electrocardiogram waveform using the number of the R waves and the degree of data concentration,
    wherein each score of the plurality of the channels increases based on the number of the R waves and the degree of the data concentration,
    wherein the each score increases more when the R waves are counted 5 times per 2 seconds than when the R waves are counted 9 times per 2 seconds, and
    wherein the each score increases more when more data signals are contained in a section having a highest number of data signals among the multiple sections.

2. The electrocardiogram waveform measurement system according to claim 1, wherein the electrodes are each configured as fabric electrodes,
    wherein the microcontroller is further configured to:
        detect a portion that deviates from the dynamic range; and
        detect an amplitude of the electrocardiogram waveform,
    wherein the electrocardiogram waveform is generated for each of the combinations using the measurement values acquired in a predetermined period of time by the fabric electrodes,
    wherein, from the plurality of channels, a channel at which the number of the R waves is within a predetermined range is selected with higher priority than a channel at which the number of the R waves deviates from the predetermined range,
    wherein, from the plurality of channels, a channel that exhibits a higher degree of data concentration is selected with higher priority than a channel that exhibits a lower degree of data concentration,
    wherein, from the plurality of channels, a channel that does not deviate from a dynamic range is selected with higher priority than a channel that deviates from the dynamic range, and
    wherein, from the plurality of channels, a channel that provides an electrocardiogram waveform having a larger amplitude is selected with higher priority than a channel that provides an electrocardiogram waveform having a smaller amplitude.

3. An electrocardiogram waveform measurement method for measuring an electrocardiogram waveform using a plurality of electrodes fixed to an article of clothing, the electrocardiogram waveform measurement method comprising:
    electrocardiogram waveform measuring in which, with a combination of a part of the plurality of electrodes as a channel, an electrocardiogram waveform is generated using measurement values acquired by the electrodes for each of a plurality of channels;
    R wave processing in which R waves in the electrocardiogram waveform are counted for each channel to acquire a number of the R waves;
    degree-of-concentration calculation in which a degree of data concentration is calculated for each channel in a dynamic range of the electrocardiogram waveform, wherein the dynamic range is divided into multiple sections; and channel selecting in which a combination of the electrodes having a highest score among the plurality of the channels is selected to measure the electrocardiogram waveform using the number of the R waves counted in the R wave processing and the degree of data concentration calculated in the degree-of-concentration calculation, wherein each score of the plurality of the channels increases based on the number of the R waves and the degree of the data concentration, wherein the each score increases more when the R waves are counted 5 times per 2 seconds than when the R waves are counted 9 times per 2 seconds, and wherein the each score increases more when more data signals are contained in a section having a highest number of data signals among the multiple sections.

* * * * *